(12) United States Patent
Brady et al.

(10) Patent No.: US 7,830,507 B2
(45) Date of Patent: Nov. 9, 2010

(54) SPATIALLY PATTERNED SUBSTRATES FOR CHEMICAL AND BIOLOGICAL SENSING

(75) Inventors: David J. Brady, Durham, NC (US); Michael E. Sullivan, Raleigh, NC (US); Prasant Potuluri, Durham, NC (US)

(73) Assignee: Optopo Inc., Morrisville, NC (US)

( * ) Notice: Subject to any disclaimer, the term of this patent is extended or adjusted under 35 U.S.C. 154(b) by 697 days.

(21) Appl. No.: 11/352,298

(22) Filed: Feb. 13, 2006

(65) Prior Publication Data
US 2007/0188749 A1 Aug. 16, 2007

(51) Int. Cl.
C12M 1/34 (2006.01)
G01J 3/04 (2006.01)
(52) U.S. Cl. .................... 356/328; 435/7.1; 436/171
(58) Field of Classification Search .............. None
See application file for complete search history.

(56) References Cited

U.S. PATENT DOCUMENTS

| | | | |
|---|---|---|---|
| 4,514,495 A * | 4/1985 | Schalkowsky et al. | 435/32 |
| 4,615,619 A | 10/1986 | Fateley | |
| 4,750,834 A | 6/1988 | Fateley | |
| 4,799,795 A | 1/1989 | Fateley | |
| 4,856,897 A | 8/1989 | Fateley | |
| 5,257,086 A | 10/1993 | Fateley | |
| 5,488,474 A | 1/1996 | Fateley | |
| 6,046,808 A | 4/2000 | Fateley | |
| 6,128,078 A | 10/2000 | Fateley | |
| 6,165,734 A * | 12/2000 | Garini et al. | 435/7.21 |
| 6,208,413 B1 | 3/2001 | Diehl et al. | |
| 6,392,748 B1 | 5/2002 | Fateley | |
| 6,859,275 B2 | 2/2005 | Fateley | |
| 7,092,089 B2 * | 8/2006 | Filippini et al. | 356/328 |
| 2002/0057431 A1 | 5/2002 | Fateley | |
| 2003/0062422 A1 | 4/2003 | Fateley | |
| 2004/0218172 A1 | 11/2004 | DeVerse | |
| 2005/0024640 A1 | 2/2005 | Fateley | |
| 2005/0163659 A1 * | 7/2005 | Duveneck et al. | 422/61 |
| 2005/0243312 A1 | 11/2005 | Geshwind | |
| 2005/0254709 A1 | 11/2005 | Geshwind | |

(Continued)

FOREIGN PATENT DOCUMENTS

WO WO2004044536 A1 5/2004

OTHER PUBLICATIONS

Bellamy, Mortensen, Orr, Marshall, Paukstelis, Hammaker, and Fateley, "Hadamard- and Fourier-transform infrared Imaging and spectrometry." Mikrochimica Acta (Supplementum), vol. 14, pp. 759-761, 1997.

(Continued)

*Primary Examiner*—Gregory J Toatley, Jr.
*Assistant Examiner*—Rebecca C Slomski
(74) *Attorney, Agent, or Firm*—John R. Kasha; Kasha Law LLC (57) ABSTRACT

A system and method are provided for imaging a test substrate having a test surface that is configured to enable spectroscopic detection of one or more chemical or biological species, wherein the test surface includes a testing site disposed thereon according to a predetermined spatial pattern. The test substrate is provided in an image plane or a Fourier Transform plane of a sensor. The invention provides high throughput and high spectral resolution.

35 Claims, 7 Drawing Sheets

U.S. PATENT DOCUMENTS

2005/0270528 A1    12/2005    Geshwind
2006/0092414 A1     5/2006    Geshwind
2006/0250613 A1*   11/2006    Demuth et al. .............. 356/301
2007/0081158 A1*    4/2007    Brady et al. ................ 356/310

OTHER PUBLICATIONS

DeVerse, Hammaker, and Fateley, "Hadamard transform Raman imagery with a digital micro-mirror array," Vibrational Spectroscopy, vol. 19. pp. 177-186, 1999.

DeVerse, Hammaker, Fateley, Graham, and Tate, "Spectrometry and imaging using a digital micromirror array." American Laboratory, vol. 30, p. 112S, 1998.

Golay, "Static multislit spectrometry and its application to the panoramic display of infrared spectra," J. Opt. Soc. Am., vol. 41, pp. 468-472, 1951.

Mende, Claflin, Rairden, and Swenson, "Hadamard spectroscopy with a two-dimensional detecting array," Applied Optics. vol. 32, pp. 7095-7105, 1993.

Murzin, Murzina, and Shlishevsky, "New grilles for Girard spectrometers," Applied Optics, vol. 24, pp. 3625-3630, 1985.

Shlishevskii, "Methods of high-aperture grid spectroscopy." Journal of Optical Technology, vol. 69 pp. 342-353, 2002.

Brady, "Multiplex sensors and the constant radiance theorem," Optics Letters, vol. 27. pp. 16-18, 2002.

Jacquinot, "New developments in interference spectroscopy," Rep. Prog. Phys., vol. 23, pp. 267-312, 1960.

Golay, "Multislit Spetrometry," J. Opt Soc. Am., vol. 39, pp. 437-444, 1949.

Ibbett, Aspinall, and Grainger, "Real-time multiplexing of dispersed spectra in any wavelength region," Applied Optics, vol. 7, p. 1089, 1988.

Decker and Harwitt, "Sequential encoding with multislit spectrometers," Applied Optics, vol. 7, p. 2205, 1968.

Decker, "Experimental realization of the multiplex advantage with a Hadamard-transform spectrometer," Applied Optics, vol. 10, pp. 510-514, 1971.

Hansen and Strong, "High resolution Hadamard transform spectrometer," Applied Optics, vol. 11, pp. 502-506, 1972.

Swift, Wattson, Decker, Paganetti, and Harwitt, "Hadamard transform imager and imaging spectrometer," Applied Optics, vol. 15, pp. 1595-1609, 1976.

Riesenberg and Dillner, "Hadamard imaging spectrometer with micro slit matrix," Proc. SPIE, vol. 3753, pp. 203-213, 1999.

Deverse, Hammaker, and Fateley, "Realization of the Hadamard multiplex advantage using a programmable optical mask in a dispersive flat-field near-infrared spectrometer," Applied Spectroscopy, vol. 54, pp. 1751-1758, 2000.

Riesenberg, Nitzsche, and Voigt, "Hadmard encoding and other optical multiplexing," VDI Berichte, vol. 1694, pp. 345-350, 2002.

\* cited by examiner

SPATIALLY PATTERNED SUBSTRATES FOR CHEMICAL AND BIOLOGICAL SENSING

FIELD OF THE INVENTION

This invention is directed to a system and method of using spatially patterned substrates to isolate and accentuate optical signals from chemical sensors. More particularly, embodiments of the present invention use Fourier and focal plane aperture coding to produce molecule-specific scattering and image features in optically transduced chemical and biological sensors.

BACKGROUND OF THE INVENTION

Molecular detection based on the interaction of a receptor molecule and a target molecule is the basis of chemical and biological sensing. Given a molecular recognition system, however, digital transduction is the primary challenge of sensor design. Molecular interactions may change electronic, optical or acoustic properties of a sample.

Molecular interactions may modulate the scattering, fluorescence, absorption or other properties of a sample under test. Typically theses properties are monitored by placing a sample carrier in a conventional spectrometer or similar instrument. The sample carrier is typically a surface functionalized with molecular recognition agents. Sensitivity is increased by making the area of the functionalized surface as large as possible.

For a number of reasons, detection of absorption or spectral scattering features from surface interactions is difficult with conventional spectrometers. For example, the absorption features are typically weak. Further, isolation from strong background signals is not achieved.

In addition, conventional spectroscopic sensors are not well adapted to integration of spectral signals from large area samples. For example, when working with highly scattering diffuse samples or when using low light techniques such as fluorescence and Raman scattering, conventional grating-based spectrometers that use slits produce less than desirable measurement sensitivity, specificity, and selectivity.

Further, conventional slit-based spectrometers are not well suited for the large chemical interaction areas that are used in chemical and biological sensing. From a chemical and biological sensing perspective, a large surface area increases an effective volume of sample tested by maximizing a chemical interaction area. However, large surface areas are difficult to cover using conventional slit-based spectrometers.

SUMMARY

Embodiments of the present invention overcome at least some of these and other drawbacks of existing systems. Embodiments of the present invention improve sensing based on molecularly induced optical signals. For example, embodiments of the present invention enhance spectroscopic signal isolation and detection using spatial patterning of reactive areas of a testing surface. With respect to absorption, spatial patterning creates optical diffraction orders with intensity that is proportional to relevant spectral features. In the case of Raman scattering and other spectrally correlated scattering and fluorescence effects, spatial patterning enables collection of highly resolved spectral signals. In both cases, spatial patterning enables signal collection from assays that have 100 micron to 1 cm cross sections. This cross section is larger than typical sample cross sections used with conventional imaging spectrometers. Spatial patterning also enables parallel data collection from multiple assay components.

According to one embodiment of the present invention, nanoparticle sensors use nanoparticle assays to perform chemical and/or biological sensing. The nanoparticle assays include metal nanoparticles that provide a nonspecific platform for optical transduction of molecular signals. To introduce specificity to nanoparticle sensors, the surface of a substrate that receives the nanoparticle assays may be functionalized with target specific binding agents.

The nanoparticle sensors perform molecular detection by monitoring reaction dynamics as the functionalized nanoparticles are exposed to test samples that include target chemicals or biological species. During exposure, the test samples bind to the nanoparticles, which increases a density of target molecules in the nanometer-scale vicinity of a particle. The change in molecular density may be detected through changes in the optical response of nanoparticles that are induced by molecules in the test sample. For example, an increase in molecular density on the surface of a nanoparticle changes an effective index of refraction that surrounds the metal nanoparticle and shifts a localized surface plasmon resonance (LSPR) of the metal nanoparticle.

According to embodiments of the present invention, systems and methods are provided for analyzing a large test surface, wherein the test surface is generated using a surface-bound chemical test. According to one embodiment, test substrates are prepared with one or more test surfaces that include chemically active materials which are deposited in a spatial structure or pattern, where $\rho(x,y)$ represents a density of chemically active sites on the test substrate. These patterned substrates may be placed either in the image plane of a spectrometer or in the Fourier Transform plane of the spectrometer.

Embodiments of the present invention have numerous advantages over and avoid many drawbacks of conventional systems. These and other objects, features, and advantages of the invention will be apparent through the detailed description of the embodiments and the drawings attached hereto. It is also to be understood that both the foregoing general description and the following detailed description are exemplary and not restrictive of the scope of the invention. Numerous other objects, features, and advantages of the invention should now become apparent upon a reading of the following detailed description when taken in conjunction with the accompanying drawings, a brief description of which is included below.

BRIEF DESCRIPTION OF THE DRAWINGS

The drawings appended hereto are intended to illustrate contemplated embodiments of the invention. The drawings are not intended to limit the invention solely to the embodiments illustrated and described.

DETAILED DESCRIPTION

While specific embodiments of the invention are discussed herein and are illustrated in the drawings appended hereto, the invention encompasses a broader scope than the specific subject matter described and illustrated. As would be appreciated by those skilled in the art, the embodiments described herein provide but a few examples of the broad scope of the invention. There is no intention to limit the scope of the invention only to the embodiments described.

Figure 1:
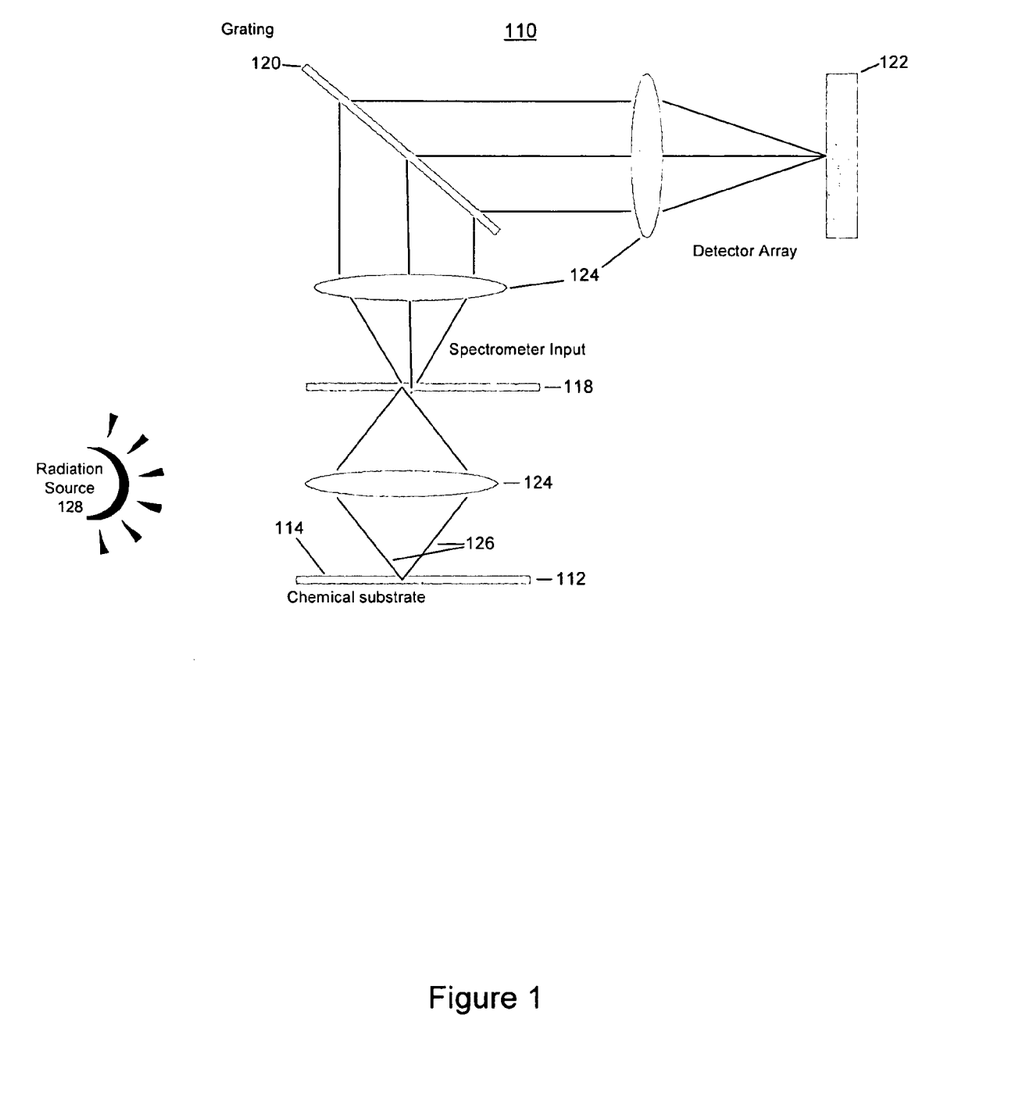
FIG. 1 is a schematic diagram of a conventional dispersive spectrometer.

FIG. 1 illustrates a conventional dispersive spectrometer 110. Spectrometer 110 may include a substrate 112 that provides a testing surface 114, a source 128, a mask 118 that includes one or more transmissive and opaque elements, a diffractive element 120, a detector array 122, one or more optical elements 124 that guide radiation generated by a source 128 within spectrometer 110, and/or other components. The term "radiation" used herein includes all types of electromagnetic radiation, such as ultraviolet (UV) radiation, visible radiation, near infrared, or other radiation. Source 128 may include a diffuse source that inherently produces a highly, spatially-multimodal optical field. For example, the source may include a spatially-extended source with an angularly-extended radiation pattern.

In conventional optical analysis, source 128 emits radiation that may be directed at substrate 112, which causes radiation 126 to radiate from substrate 112. Radiation 126 includes one or more spectral properties that are influenced by one or more chemical and/or biological species present on testing surface 114. Radiation 126 may be imaged by optical elements 124 and may be directed onto mask 118 that includes transmissive and opaque elements. Radiation 126 that impinges on mask 118 will either pass through the transmissive elements of mask 118 or be blocked by the opaque elements of mask 118. Mask 118 converts intensity information received from substrate 112 into frequency or spectral information. Optical elements 124 may direct portions of radiation 126 that pass through mask 118 onto diffractive element 120. Diffractive element 120 receives radiation from mask 118 and disperses the radiation in a linear spatial relationship based on wavelength. Diffractive element 120, which is typically a diffraction grating, diffracts radiation 126 onto detector array 122. Detector array 122 comprises rows and columns of detector elements. Detector elements may be designed to receive a different range of wavelengths from each transmissive element of mask 118 and to provide a signal that indicates an intensity of the radiation received.

Substrate 112 may include glass slides, or other substrates, having testing surface 114, such as a coating of specially prepared films. Testing surface 114 may include, for example, an assay of functionalized metal nanoparticles, wherein testing surface 114 produces a signature optical spectrum at detector array 122 when not exposed to a sample to be analyzed. The signature optical spectrum may be unique for each assay of functionalized metal nanoparticles.

In operation, substrate 112 is exposed to a test sample, such as a liquid or gas that contains target chemicals or biological species. During exposure, the target chemicals or biological species may bind to components of testing surface 114. The resulting testing surface 114 that includes chemicals or biological species bound thereon produces an optical spectrum that differs from the unique signature optical spectrum that is associated with the unexposed testing surface 114.

Conventional spectrometers may use a mask 118 having a point or an entrance slit to convert intensity information received from substrate 112 into frequency or spectral information. In order to obtain high spectral resolution, the point diameter or the entrance slit width should be small. From an optical spectroscopy perspective, a small point diameter or narrow entrance slit width that provides higher spectral resolution is preferred over a large point diameter or wide entrance slit width that provides lower spectral resolution. However, using a mask 118 having a small point diameter or a narrow entrance slit width reduces an amount of surface area that may be tested on substrate 112 at one time.

By contrast, from a chemical sensing perspective, a large surface area is preferred for substrate 112. A large surface area on substrate 112 increases an effective volume of sample tested by maximizing a chemical interaction area, and provides a sensor with greater sensitivity. Embodiments of the present invention provide an improved interface for use in optical spectrometers to analyze chemical or biological samples. As a result, embodiments of the present invention resolve an interface mismatch in conventional optical spectrometer systems having a narrow entrance slit where sampling of large surface areas for chemical and/or biological sensing is required.

Figure 2:
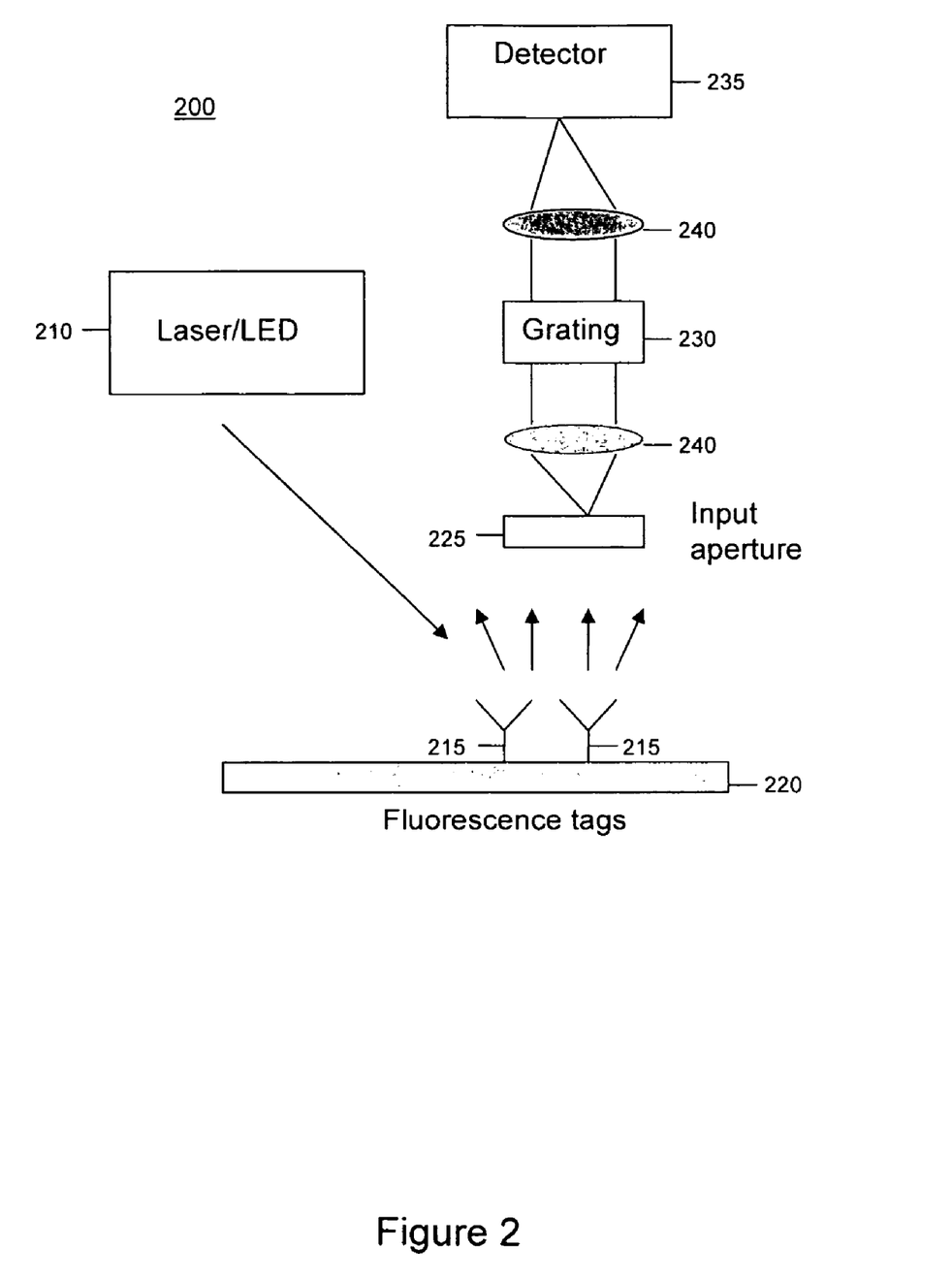
FIG. 2 is a schematic diagram of an optical apparatus for a fluorescence sensor.

Various types of sensors may be used in embodiments of the present invention to perform chemical and/or biological sensing. Such sensors include fluorescence sensors, nanoparticle sensors, and other sensors. FIG. 2 is a schematic diagram of a typical optical apparatus for a fluorescence sensor 200. In the apparatus illustrated in FIG. 2, fluorescence signals are generated using marker chemicals that are embedded in a substrate 220. Fluorescence sensor 200 includes substrate 220 having fluorescent tags 215 thereon, a source 210, a mask (input aperture) 225 that includes one or more transmissive and opaque elements, a diffractive element 230, a detector 235, one or more optical elements 240 that guide radiation within fluorescence sensor 200, and/or other components.

The fluorescence based optical sensor 200 provides high sensitivity and detects very low concentrations of analytes. Source 210 can be a laser, LED or other source, that may be used to excite analyte molecules that are bound to fluorescent tags 215. The analyte molecules may be detected in various ways. For example, the fluorescent tags 215 may start to fluoresce once the analyte molecules are bound to fluorescent tags 215. An amount of fluorescence depends on a concentration of the analyte molecule that are bound to the fluorescent tags 215.

Figure 3A:
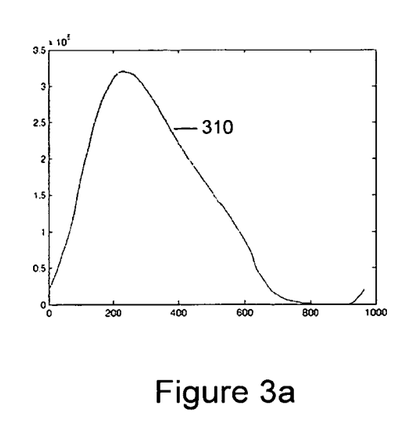
FIGS. 3a and 3b illustrate a fluorescence spectrum.
Figure 3B:
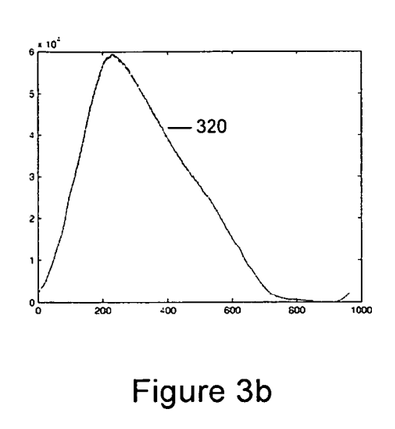

Alternatively, the fluorescent tags 215 may exhibit an initial fluorescence pattern with no analyte or change in the peak of the fluorescence from the initial fluorescence pattern depending on analyte concentration. FIGS. 3a and 3b illustrate exemplary fluorescence from Cy-5, a red-emitting cyanine dye used to tag varying concentrations of proteins. As illustrated in FIGS. 3a and 3b, once the analyte molecules bind to fluorescent tags 215, the peak of the fluorescence may shift, or an intensity of the fluorescence may change, depending on the concentration of the analyte binding to the fluorescence tags. Curve 310 illustrates a curve corresponding to a high concentration of the analyte. Curve 320 illustrates a curve corresponding to a low concentration of the analyte. Both of the above embodiments measure fluorescence using a spectrometer.

In another type of sensor, nanoparticle sensors use nanoparticle assays to perform chemical and/or biological sensing. The nanoparticle assays include metal nanoparticles that provide a nonspecific platform for optical transduction of molecular signals. To introduce specificity to nanoparticle sensors, the surface of a substrate that receives the nanoparticle assays may be functionalized with target specific binding agents.

In operation, nanoparticle sensors perform molecular detection by monitoring reaction dynamics as the functionalized nanoparticles are exposed to test samples that include target chemicals or biological species. During exposure to the sample, the test samples bind to the nanoparticles. Such binding increases a density of target molecules in the nanometer-scale vicinity of a particle. The change in molecular density may be detected through changes in the optical response of nanoparticles that are induced by molecules in the test sample. In this case, an increase in molecular density on the surface of a nanoparticle changes an effective index of refraction that surrounds the metal nanoparticle and shifts a localized surface plasmon resonance (LSPR) of the metal nanoparticle.

Alternatively, the change in molecular density may be detected through changes in the optical response of the test sample molecules that are induced by the nanoparticle. In this case, strong electromagnetic fields that are present in the nanometer-scale vicinity of the metal nanoparticle surface couple with an increased molecular density to amplify a spectral response from the test sample molecules. Surface enhanced Raman spectroscopy (SERS) is a preferred molecular spectroscopy in this case because Raman scattering is highly sensitive to the field intensity and highly specific to the molecular signal. Such nanoparticle sensors may be used for a variety of applications, including medical diagnostics, drug discovery, proteomics and environmental detection of biological agents, or other applications.

Figure 4:
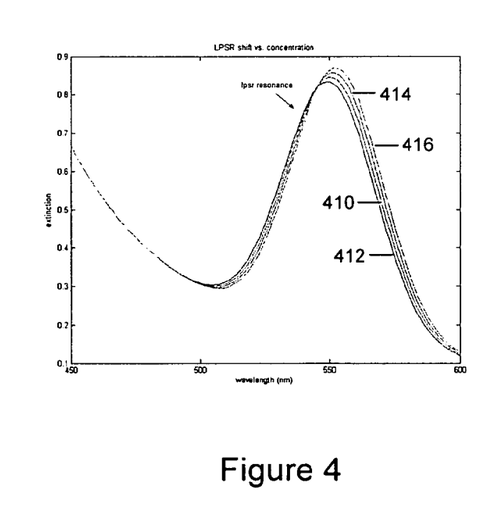
FIG. 4 illustrates an extinction spectra.

Regarding changes in the optical response of nanoparticles that are induced by molecules in the test sample, localized surface plasmon resonance (LSPR) creates a strong feature in the absorption and scattering spectrum of metal nanoparticle assays. FIG. 4 is a graphical illustration of exemplary extinction spectra versus target concentration for nanoparticle assays. As surface agents on the nanoparticles react with a test sample containing target chemicals or biological species, the LSPR extinction spectrum shifts and deforms as illustrated in FIG. 4. Each curve 410, 412, 414, 416 represents the simulation data of the saturation extinction for a particular concentration. LSPR is sensitive to nanoparticle size and shape, as well as the permittivity of the surrounding medium. The dynamics and magnitude of this transformation are informative of the test sample concentration present in the assay. Typically, LSPR produces an optical extinction band of width 30-50 nm for a given nanoparticle. Resonances shift by 3-5 nm on binding, continuously shifting in proportion to binding events. An LSPR biosensor measures concentration of the target molecule by monitoring the spectral shift as the target assay reacts with the functionalized nanoparticles.

Regarding changes in the optical response of the test sample molecules that are induced by the nanoparticle, surface enhanced Raman spectroscopy (SERS) is an inelastic scattering process that is linear in the optical intensity. Boundary conditions on nanoparticles induce very strong electromagnetic fields in the immediate vicinity of the nanoparticle. As a result of the strong electromagnetic fields, the Raman signal generated in the vicinity of a nanoparticle may be orders of magnitude higher than a background signal of homogeneous spaces. SERS is preferred in these types of cases because it produces spectra that are highly characteristic of the scattering molecule and highly selective of the nanoparticle environment.

Figure 5:
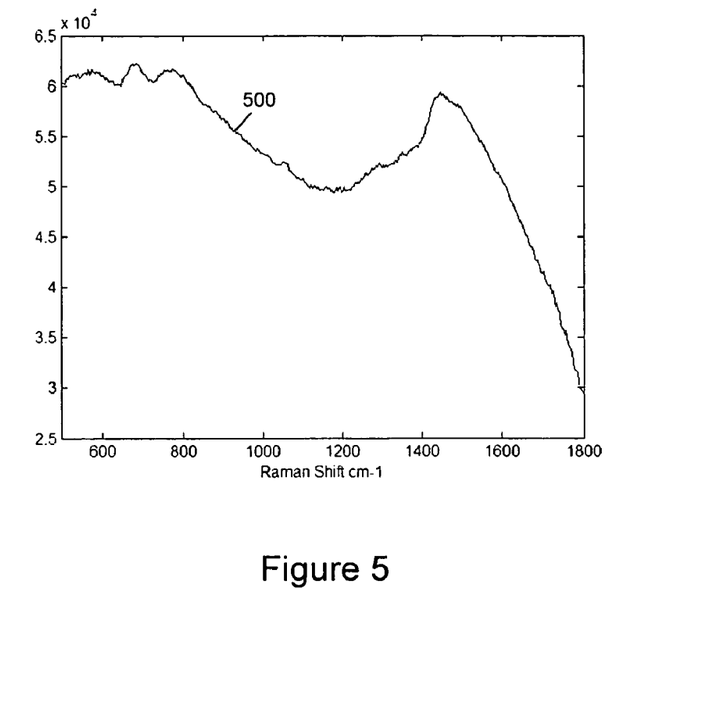
FIG. 5 illustrates a Raman spectrum.
Figure 6:
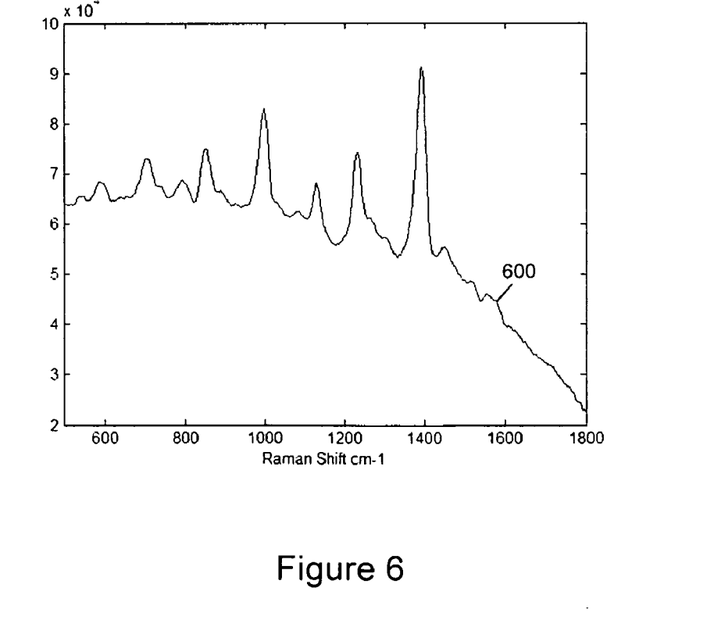
FIG. 6 illustrates a Raman spectrum.

FIGS. 5 and 6 illustrate SERS spectra that may be used to detect low concentrations of a target molecule. Curve 500 illustrates the Raman spectrum of biotin that is attached to Gold nanoparticles on a substrate. As illustrated in FIG. 5, biotin does not produce any strong Raman peaks. However, when a test sample that includes a molecule such as Streptavidin is added to the substrate, Streptavidin binds to biotin. The resulting combination has significant Raman peaks as illustrated in curve 600 in FIG. 6. The peak intensities in curve 600 are proportional to the concentration of Streptavidin. In this example, the concentration of Streptavidin is 0.1 µg/ml. Thus, sensitivities may be achieved on a pico-molar order. Most molecules evince a SERS enhancement. When a total Raman intensity is considered from a bulk sample, the SERS enhancement is not orders of magnitude above the background. In addition, SERS may detect molecules having dense degeneracies, such as DNA. Alternatively, SERS may detect the density of bonding events through disruption of Raman signals from the surface bound binding molecule.

SERS is preferred for highly sensitive and highly specific detection of low molecular concentrations, whereas LSPR may generate a stronger effect at higher concentrations. Target specific binding on nanoparticles, when combined with SERS, enables Raman analysis of molecules at several orders of magnitude lower concentration than conventional Raman spectroscopy.

During chemical or biological sensing, substrate 112 is exposed to a test sample. Chemical and/or biological species that are present in the test sample bind to the testing surface 114. The interaction between the chemical and/or biological species and testing surface 114 may modulate, for example, the absorption spectrum of radiation that passes through substrate 112, the spectrum of radiation that is scattered by the testing surface 114 or the spectrum of radiation that is emitted from testing surface 114. For example, in one embodiment, the absorption spectrum of nanoparticle assays may be modulated by changes in the localized surface plasmon resonance (LSPR) that is associated with the nanoparticles. In another embodiment, the scattering spectrum of nanoparticle assays may be modulated by changes in the surface enhanced Raman spectrum (SERS). In yet another embodiment, fluorescence signals may be generated by marker chemicals embedded in the film.

In the above cases, spectroscopic signal isolation and detection is enhanced by spatially patterning reactive areas of testing surface 114. Regarding absorption, spatial patterning creates optical diffraction orders with intensity that is proportional to relevant spectral features. In the case of Raman scattering, and other spectrally correlated scattering and fluorescence effects, spatial patterning enables collection of highly resolved spectral signals. In both cases, spatial patterning enables signal collection from assays that have 100 micron to 1 cm cross sections. This cross section is much larger than is typical with imaging spectrometers. Spatial patterning also enables parallel collection of data from multiple assay components.

U.S. provisional application Nos. 60/644,522, filed on Jan. 19, 2005, and 60/705,173, filed on Aug. 4, 2005, disclose systems and methods for achieving high throughput and high spectral resolution by replacing the slit of conventional dispersive spectrometers with a spatial filter. These provisional applications disclose static two-dimensional aperture coding for multimodal multiplex spectroscopy using coded patterns on mask 118, including independent column code patterns, orthogonal column code patterns, or other patterns. These provisional applications disclose making the area passed by the aperture arbitrarily large through the use of coded patterns in the aperture. Copies of these provisional applications are attached hereto as appendix A.

According to embodiments of the present invention, systems and methods are provided for analyzing a large test surface, wherein the test surface is generated using a surface-bound chemical test agent. According to one embodiment, substrates 112 are prepared with one or more test surfaces 114 that include chemically active materials which are deposited in a spatial structure, where $\rho(x,y)$ represents a density of chemically active sites on substrate 112. The spatial structure is also referred to herein as a spatial pattern. These patterned substrates may be placed either in the image plane of a spectrometer or in the Fourier Transform plane of the spectrometer.

Figure 7:
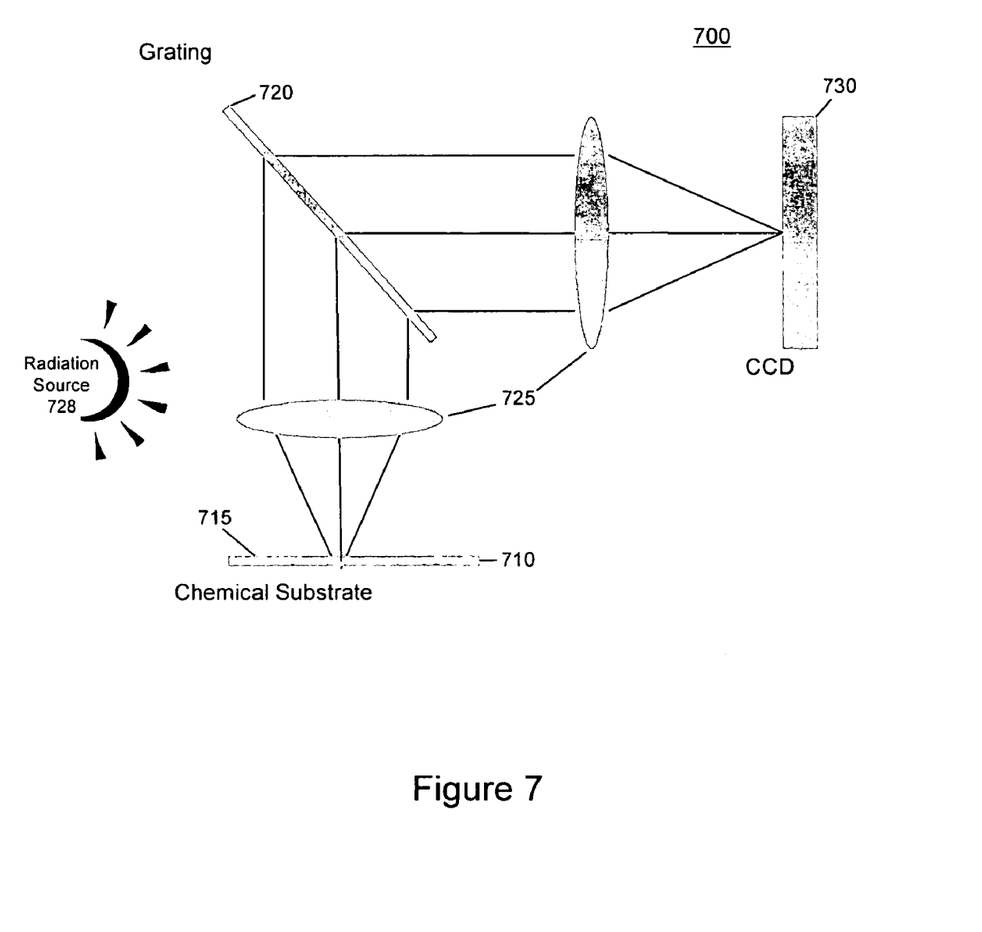
FIG. 7 illustrates a patterned substrate spectrometer according to one embodiment of the invention.

FIG. 7 is a schematic diagram of a patterned substrate spectrometer 700 according to an embodiment of the present invention. A patterned substrate spectrometer 700 is provided with a patterned test substrate 710 located in a position typically occupied by a mask, such as for example, illustrated by mask 118 in FIG. 1. According to another embodiment of the invention, diffractive element 720 may be replaced with patterned test substrate 710. Patterned substrate spectrometer 700 also may include a source 728, a diffractive element 720, a detector array 730 such as a CCD, one or more optical elements 725 that guide radiation within spectrometer 700, and/or other components. Test substrate 710 may include a testing surface 715 that is placed thereon. As will be described, replacing the mask or dispersive element 720 with patterned test substrate 710 allows a patterned substrate spectrometer to achieve high throughput, or wide entendue.

For both nanoparticle-based sensors or Fluorescence-based sensors, one or more test substrates 710 may be patterned instead of patterning the mask. Such patterns include orthogonal column codes, independent column codes and other codes.

According to one embodiment of the invention, $\rho(x,y)$ represents the density of chemically active sites on test surface 715. $S(\lambda)$ represents a spectrum that is radiated by test substrate 710 that has not been exposed to a test sample. The chemically active sites, such as nanoparticles or fluorescent markers, may radiate via Raman scattering, absorbance or fluorescence, depending on the sensor used and the excitation methodology. In all the cases, however, the spectrum that is radiated by test substrate 710 is measured.

In operation, when a molecule of interest binds to test surface 715, the radiated spectrum is modified due to a change in several properties such as amplitude, energy, refractive index, polarization, or other properties. The spectrum resulting from exposure of the patterned test substrate to a test sample is denoted $S'(\lambda)$. For analysis purposes, the parameters of the spectrum may be correlated with a concentration of the analyte of interest.

According to one embodiment, if detector array 730 measures mean values of $S(\lambda)$ and $S'(\lambda)$, then the concentration of the target molecule may be estimated. $S'(\lambda)$ represents the spectrum measured at detector array 730 after the test substrate has been exposed to a test sample. For a spatial distribution pattern of $\rho(x,y)$, the optical intensity detected by the detector array is:

$$g(x', y') = \int \int \int d\lambda dx dy H(x, y, \lambda) S(x, y, \lambda) \quad (1)$$
$$= \int \int \int d\lambda dx dy H(x, y, \lambda) S(\lambda) \rho(x, y)$$

where $H(x,y,\lambda)$ represents a kernel that describes a propagation through spectrometer 700. For a dispersive spectrometer with unit magnification and linear dispersion a in the x-direction, $$H(x,y,\lambda) = \delta(y-y')\delta(x-(x'-\alpha\lambda)) \quad (2)$$

where $\alpha$ is a constant determined by a period of diffractive element 720 and an effective focal length of the optical system. Substituting equation (2) into equation (1) and integrating over x and y yields an optical intensity that is detected by detector array 730 is:

$$g(x',y') = \int \rho(x'-\alpha\lambda, y') S(\lambda) d\lambda \quad (3)$$

According to one embodiment, a mean spectrum $S(\lambda)$ before exposure to a test sample may be estimated across the entire test substrate 710 from the measured values of $g(x',y')$. To estimate a mean spectrum from the intensity profile, an analysis function $\rho'(x,y)$ and equation 4 below are used, wherein a double prime represents an estimate function.

$$E(x',x'') = \int dy' \rho'(x'',y') g(x',y') \quad (4)$$

If $\rho(x,y)$ and $\rho'(x,y)$ are constructed such that $$\int \rho(x,y) \rho'(x'',y) dy = \delta(x-x'') \quad (5)$$

then the estimate $E(x',x'')$ becomes $$E(x', x'') = \int \int S(\lambda) \rho(x' - \alpha\lambda, y') \rho(x'', y') dy' d\lambda \quad (6)$$
$$= \int S(\lambda) \delta(x' - x'' - \alpha\lambda) d\lambda$$
$$= S\left(\lambda = \frac{x' - x''}{\alpha}\right)$$

If all values of $E(x', x'')$ are averaged such that $x'-x''=\alpha\lambda$, then an estimate for the mean value of $\overline{S}(\lambda)$ is obtained. Thus, with appropriately designed spatial patterns on test substrate 710, intensity distribution may be converted on detector array 730 into an estimate of the mean spectrum across the entire chemically active test substrate 710. The binding of chemical and/or biological elements to test surface 715 alters the spectrum $S(\lambda)$ to yield $\overline{S}'(\lambda)$. The spectrum change may be correlated to a concentration of the analyte of interest.

Figure 8:
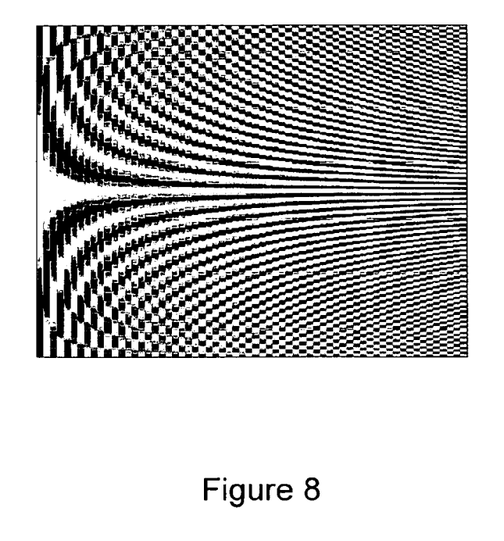
FIG. 8 illustrates a density distribution pattern for a substrate according to one embodiment of the invention.

Spatial patterns of the type described above are discussed in detail in provisional application Nos. 60/644,522 and 60/705,173. FIG. 8 illustrates an exemplary density distribution of chemically active substances on a substrate according to an orthogonal column code based on harmonic functions.

In FIG. 8, the spatial pattern on the substrate takes the form $$\rho(x, y) \in \left\{\frac{1}{2}\left(1 + \cos\left(m\frac{y\pi}{Y}\right)\right)\right\}, m \in Z \quad (7)$$

A corresponding analysis function is $$\rho(x'', y) \in \left\{2\cos\left(m\frac{y\pi}{Y}\right)\right\}, m \in Z \quad (8)$$

According to the invention, spectrometer 700 illustrated in FIG. 7 measures the mean spectrum $\overline{S}(\lambda)$ and $\overline{S}'(\lambda)$ of the test substrate 710 at the substrate and at the detector array 730, before and after the binding of the target molecules. The change in $\overline{S}(\lambda)$ is correlated with the concentration of the target molecule so that spectrometer 700 may be calibrated to estimate the concentration of the analyte of interest. This approach averages the entire test sample area, and gives a reliable estimate of the concentration.

Figure 9:
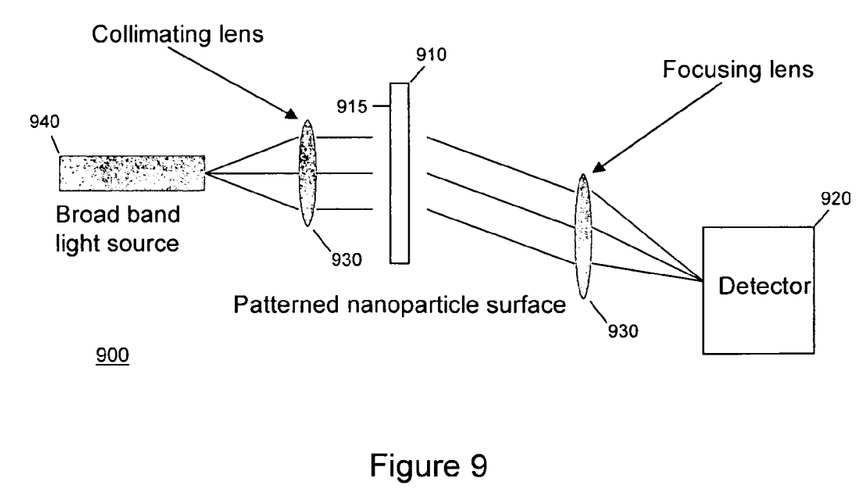
FIG. 9 illustrates a spectrometer according to another embodiment of the invention.

FIG. 9 is a schematic diagram of a patterned substrate spectrometer 900 according to another embodiment of the present invention. In spectrometer 900, test substrate 910 is placed in a location typically occupied by a diffractive element. Test substrate 910 may include a test surface 915 that is spatially patterned to generate diffraction orders. Spectrometer 900 may include a source 940, a detector 920, one or more optical elements 940/930 that guide radiation within spectrometer 900, and/or other components.

Spectrometer 900 may be used as an LSPR sensor. An LSPR sensor relies on the changes in the absorbance before and after the binding of a target molecule. As surface agents on the nanoparticle react with a target assay, the LSPR extinction spectrum shifts and deforms. The magnitude of this transformation is correlated to the target concentration in the assay. Therefore, LSPR biosensors measures the absorbance spectrum of the nanoparticles before and after the binding event. The concentration of the target molecule may be found by monitoring the spectral shift. According to an embodiment, spatial patterning of test surface 915 creates optical diffraction orders with intensity that is proportional to relevant spectral features. Spatial patterning enables signal collection from wide area assays with dimensions from 100 micron to 1 cm at a cross section, for example. The cross sectional size of test surface 915 is much larger than what is used in conventional imaging spectrometers.

In FIG. 9, broadband light source 940 illuminates test surface 915 through a collimating lens 930. Test surface 915 includes nanoparticles having a spatial distribution given by $\rho(x,y)$. In operation, the LSPR extinction spectrum $S(\lambda)$ induced by the surface agents on the nanoparticles is estimated. A modified spectrum $S'(\lambda)$ is also measured as the target assay reacts with the functionalized nanoparticles. The concentration of the target assay can be estimated using the change in the spectra.

Test substrate 910 may have an effective transmission function given by, $$t(x, y) = \sqrt{S(\lambda)}\, \rho(x, y) \quad (9)$$

where the intensity transmission across the substrate is $S(\lambda)$ and where the amplitude is modulated by $\sqrt{S(\lambda)}$. According to known diffraction theory, the diffracted field after test surface 910 patterned with nanoparticles is given by the spatial Fourier transform of the test surface's transmission function:

$$E(u, v) = F \cdot T\{t(x, y)\}\big|_{u=\frac{x'}{\lambda F}, v=\frac{y'}{\lambda F}} \quad (10)$$

$$= \sqrt{S(\lambda)} \times F \cdot T\{\rho(x, y)\}$$

In a simple case where $$\rho(x, y) = \cos(\gamma x) \quad (11)$$

Then,

-continued $$E(u, v) = \sqrt{S(\lambda)}\, F \cdot T\{\rho(x, y)\}\big|_{u=\frac{x'}{\lambda F}, v=\frac{y'}{\lambda F}} \quad (11)$$

$$= \sqrt{S(\lambda)} \int \cos(\gamma x) e^{-i2\pi u x} dx$$

$$\approx \sqrt{S(\lambda)}\, \delta(2\pi u - \gamma)\big|_{u=\frac{x'}{\lambda F}}$$

$$\approx \sqrt{S(\lambda)}\, \delta\left(\frac{2\pi x'}{\lambda F} - \gamma\right)$$

$$\approx \sqrt{S(\lambda)}\, \delta\left(\lambda - \frac{2\pi}{\gamma F}x'\right)$$

$$\approx \sqrt{S(\lambda)}\, \delta(\lambda - g x')$$

where g is a constant determined by F and the effective focal length of the optical system x' and y' are the coordinates in the detector plane.

Thus intensity distribution on detector 920 is $$I(x', y') = \langle E^* E \rangle \approx S(\lambda)\delta(\lambda - g x') \quad (12)$$

The distribution on detector 920 is a horizontal line pattern whose intensity profile follows the spectrum of the substrate $S(\lambda)$. The resolution of the system depends on the pixel pitch $\Delta\rho$ and the factor g given by $$\Delta\lambda = g\Delta p \quad (13)$$

The intensity pattern changes depending on whether a target molecule is bound to the substrate or not. An estimate of $S(\lambda)$ and $S'(\lambda)$ may be measured from these values which results in an estimate for the concentration of the target molecule.

Spatial patterning also enables parallel collection of sensor data from multiple assay components. In such an embodiment of the present invention, test surface cam be configured to support multiple analytes that bind to different target molecules and produce a characteristic spectrum $\psi_i(\lambda)$, depending on the analyte and the target molecule. The transmission function of such a substrate is given by $$t(x, y) = \sum_i S_i(\lambda) \rho_i(x, y) \quad (14)$$

where $\rho_i(x,y)$ is the density distribution of $i^{th}$ analyte. According to one embodiment, test surface 915 may be made to support different analytes have different frequencies, such that $$\rho_i(x, y) = \cos\left(\sum_i \gamma_i x + \varphi_i y\right) \quad (15)$$

For such a spatial pattern, the diffracted field distribution is given by, $$E(u, v) = F \cdot T\{t(x, y)\}_{u=\frac{x'}{\lambda F}, v=\frac{y'}{\lambda F}} \quad (16)$$

$$= F \cdot T\left\{\sum_i \sqrt{S_i(\lambda)}\, \rho_i(x, y)\right\}$$

-continued $$\approx \sum_i \sqrt{S_i(\lambda)} \delta(\lambda - g_i x') \delta(\lambda - h_i y')$$

The intensity distribution on detector 920 is given by $$I(x', y') = \langle E^* E \rangle \quad (17)$$
$$= \sum_i S_i(\lambda) \delta(\lambda - g_i x') \delta(\lambda - h_i y')$$

The different analytes produce intensity patterns along different orientations on detector 920, based on the spatial frequency that is used to encode the different functionalized nanoparticles on the substrate. For example, the jth analyte produces along the line given by $\lambda = g_j x' = h_j y'$ or along $$y' = \frac{h_j}{g_j} x'.$$

Thus, if each functionalized nanoparticle is designed to bind to a different target analyte, the concentrations of multiple target analytes may be uniquely estimated in a single operation. While LSPR spectroscopy is generally a nonselective sensor platform, spatially patterning test surface 915 provides a high degree of analyte selectivity. According to one embodiment, the invention provides a 1000× performance advantage in measuring diffuse samples.

Figure 10:
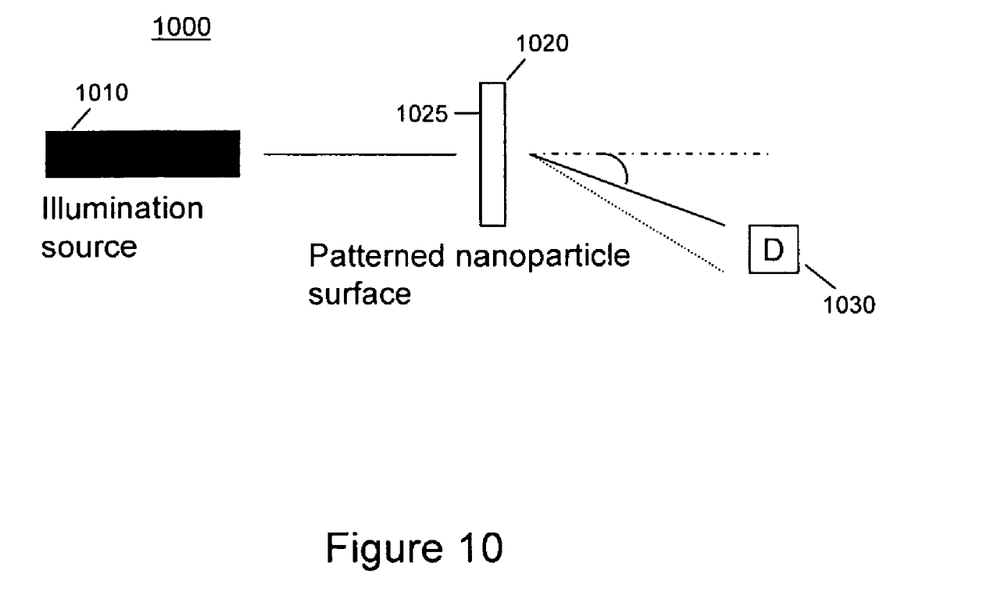
FIG. 10 illustrates a set-up that may be used to determine scattering properties of a spatially patterned nanoparticle substrate.

FIG. 10 illustrates an embodiment that may be used to determine scattering properties of spatially patterned nanoparticle substrates. System 1000 may include an illumination source 1010, a test substrate 1020 having a test surface 1025, a detector 1030, and/or other components. Detector 1030 may be positioned to capture the diffraction pattern radiating from test substrate 1010.

While the preferred forms of the invention have been disclosed, it will be apparent to those skilled in the art that various changes and modifications may be made that will achieve some of the advantages of the invention without departing from the spirit and scope of the invention. For example, the system may be configured to support a plurality of languages, among other features. It will be apparent to those reasonably skilled in the art that other components performing the same function may be suitably substituted. Further, the methods of the invention may be achieved in either all software implementations, using the appropriate processor instructions, or in hybrid implementations that utilize a combination of hardware logic and software logic to achieve the same results. Therefore, the scope of the invention is to be determined solely by the appended claims.

What is claimed is:

1. A patterned substrate spectrometer, comprising:
a test substrate;
a spatial pattern of chemically active substances for binding chemical or biological samples distributed across the test substrate according to a mathematical function;
a diffractive element;
a detector array;
a radiation source that emits radiation onto the spatial pattern;
one or more optical components that guide radiation radiated by the spatial pattern from the test substrate through the diffractive element and onto the detector array; and
a processor that receives an optical intensity from the detector array and calculates a mean spectrum of the spatial pattern from the optical intensity and the mathematical function.

2. The spectrometer of claim 1, further comprising
a test sample that binds to the spatial pattern, wherein the processor receives a second optical intensity from the detector array and calculates a second mean spectrum of the spatial pattern from the second optical intensity and the mathematical function.

3. The spectrometer of claim 2, wherein the test sample includes a chemical species.

4. The spectrometer of claim 2, wherein the test sample includes a biological species.

5. The spectrometer of claim 2, wherein the processor correlates a change between the mean spectrum and the second mean spectrum to a concentration of the test sample.

6. The spectrometer of claim 1, wherein the chemically active substance includes fluorescent tags.

7. The spectrometer of claim 1, wherein the chemically active substance includes nanoparticle assays.

8. The spectrometer of claim 1, wherein the detector array detects Raman scattering.

9. The spectrometer of claim 1, wherein the detector array detects localized surface plasmon resonance.

10. The spectrometer of claim 1, wherein the detector array detects fluorescence.

11. The spectrometer of claim 1, wherein the mathematical function includes a harmonic function.

12. A patterned substrate spectrometer, comprising:
a test substrate;
a spatial pattern of chemically active substances for binding chemical or biological samples distributed across the test substrate according to a mathematical function to generate diffraction orders;
a detector array;
a radiation source that emits radiation;
one or more optical components that guide radiation radiated by the radiation source through the spatial pattern and onto the detector array; and
a processor that receives an optical intensity from the detector array and calculates a mean spectrum of the spatial pattern from the optical intensity and the mathematical function.

13. The spectrometer of claim 12, further comprising
a test sample that binds to the spatial pattern, wherein the processor receives a second optical intensity from the detector array and calculates a second mean spectrum of the spatial pattern from the second optical intensity and the mathematical function.

14. The spectrometer of claim 13, wherein the test sample includes a chemical species.

15. The spectrometer of claim 13, wherein the test sample includes a biological species.

16. The spectrometer of claim 13, wherein the processor correlates a change between the mean spectrum and the second mean spectrum to a concentration of the test sample.

17. The spectrometer of claim 12, wherein the chemically active substance includes fluorescent tags.

18. The spectrometer of claim 12, wherein the chemically active substance includes nanoparticle assays.

19. The spectrometer of claim 12, wherein the detector array detects Raman scattering.

20. The spectrometer of claim 12, wherein the detector array detects localized surface plasmon resonance.

21. The spectrometer of claim 12, wherein the detector array detects fluorescence.

22. The spectrometer of claim 12, wherein the mathematical function includes a harmonic function.

23. A method for calculating a concentration of a test sample using a patterned substrate spectrometer, comprising:
   distributing a spatial pattern of chemically active substances for binding chemical or biological samples across a test substrate of the patterned substrate spectrometer according to a mathematical function;
   detecting a first optical intensity radiated by the spatial pattern using a detector array of the patterned substrate spectrometer;
   receiving the first optical intensity from the detector array using a processor;
   calculating a first mean spectrum of the spatial pattern from the first optical intensity and the mathematical function using the processor;
   binding a test sample to the spatial pattern;
   detecting a second optical intensity radiated by the test sample bound to the spatial pattern using a detector array;
   receiving the second optical intensity from the detector array using a processor;
   calculating a second mean spectrum of the spatial pattern from the second optical intensity and the mathematical function using the processor; and
   calculating a concentration of the test sample from a difference between the first mean spectrum and the second mean spectrum using the processor.

24. The method of claim 23, wherein the test substrate is located in an image plane of the patterned substrate spectrometer.

25. The method of claim 23, wherein the test substrate is located in a Fourier transform plane of the patterned substrate spectrometer.

26. The method of claim 23, wherein the test sample includes a chemical species.

27. The method of claim 23, wherein the test sample includes a biological species.

28. The method of claim 23, wherein the chemically active substance includes fluorescent tags.

29. The method of claim 23, wherein the chemically active substance includes nanoparticle assays.

30. The method of claim 23, wherein the detector array detects Raman scattering.

31. The method of claim 23, wherein the detector array detects localized surface plasmon resonance.

32. The method of claim 23, wherein the detector array detects fluorescence.

33. The method of claim 23, wherein the mathematical function includes a harmonic function.

34. The method of claim 23, wherein the spatial pattern is selected to enhance spectral signal isolation and detection during spectroscopic detection.

35. The method of claim 23, wherein the spatial pattern enables the spectroscopic detection based on a single spectroscopic image of the test substrate.

* * * * *